United States Patent [19]
Jones et al.

[11] 3,940,251
[45] Feb. 24, 1976

[54] APPARATUS FOR DETECTING OR MEASURING A CONSTITUENT OF A GAS

[76] Inventors: Thomas Parry Jones, 20 South Rd., Sully, Glamorgan, Wales; Basil Martin Wright, Scots Hill House, Croxley Green, Rickmansworth, Herts, England

[22] Filed: Sept. 24, 1973

[21] Appl. No.: 399,944

[30] Foreign Application Priority Data
Sept. 26, 1972 United Kingdom............... 44506/72

[52] U.S. Cl............................. 23/254 E; 23/255 E
[51] Int. Cl.².................. G01N 27/52; G01N 33/16
[58] Field of Search........... 23/254 E, 232 E, 255 E, 23/232 R, 254 R; 73/27

[56] References Cited
UNITED STATES PATENTS

| | | | |
|---|---|---|---|
| 3,117,843 | 1/1964 | Baker | 23/254 E |
| 3,342,558 | 9/1967 | Reinecke | 23/254 E X |
| 3,600,134 | 8/1971 | Noller | 23/254 E |
| 3,622,278 | 11/1971 | Elzinga | 23/232 R |
| 3,764,270 | 10/1973 | Collier et al. | 23/255 E |

Primary Examiner—Robert M. Reese
Attorney, Agent, or Firm—Woodhams, Blanchard and Flynn

[57] ABSTRACT

Apparatus for detecting alcohol vapour in a gas, such as exhaled breath. The apparatus comprises a detachable mouthpiece through which a person exhales. The mouthpiece includes a vent for venting some exhaled breath to atmosphere and an outlet port connected to a sensor which provides an electrical output dependent upon the amount of alcohol in the breath sample. A piston and cylinder valve assembly is provided for introducing a predetermined amount of the sample into the sensor at a time dictated by an operator. A calibrated meter, which may be analogue or digital is connected to the sensor to indicate the amount of alcohol in the sample.

9 Claims, 2 Drawing Figures

APPARATUS FOR DETECTING OR MEASURING A CONSTITUENT OF A GAS

BACKGROUND OF THE INVENTION

The present invention relates to apparatus for detecting or measuring a constituent of a gas and is particularly but not exclusively concerned with apparatus for detecting or measuring alcohol in a gas, such as exhaled breath.

SUMMARY OF THE INVENTION

According to the present invention there is provided apparatus comprising means for introducing a sample of the gas to a sensor for providing a voltage or current output dependent upon the amount of the constituent in the gas sample and means for measuring the voltage or current generated by the sensor. Preferably the measuring means is arranged to measure the peak potential or current or some other parameter which is a function of the peak potential or current so generated.

DESCRIPTION OF THE DRAWINGS

An embodiment of the present invention will now be described by way of example and with reference to the accompanying drawings in which.

DESCRIPTION OF THE PREFERRED EMBODIMENTS

The apparatus shown in the accompanying drawing comprises a detachable tube 10 of plastics material through which a person exhales air.

Figure 1:
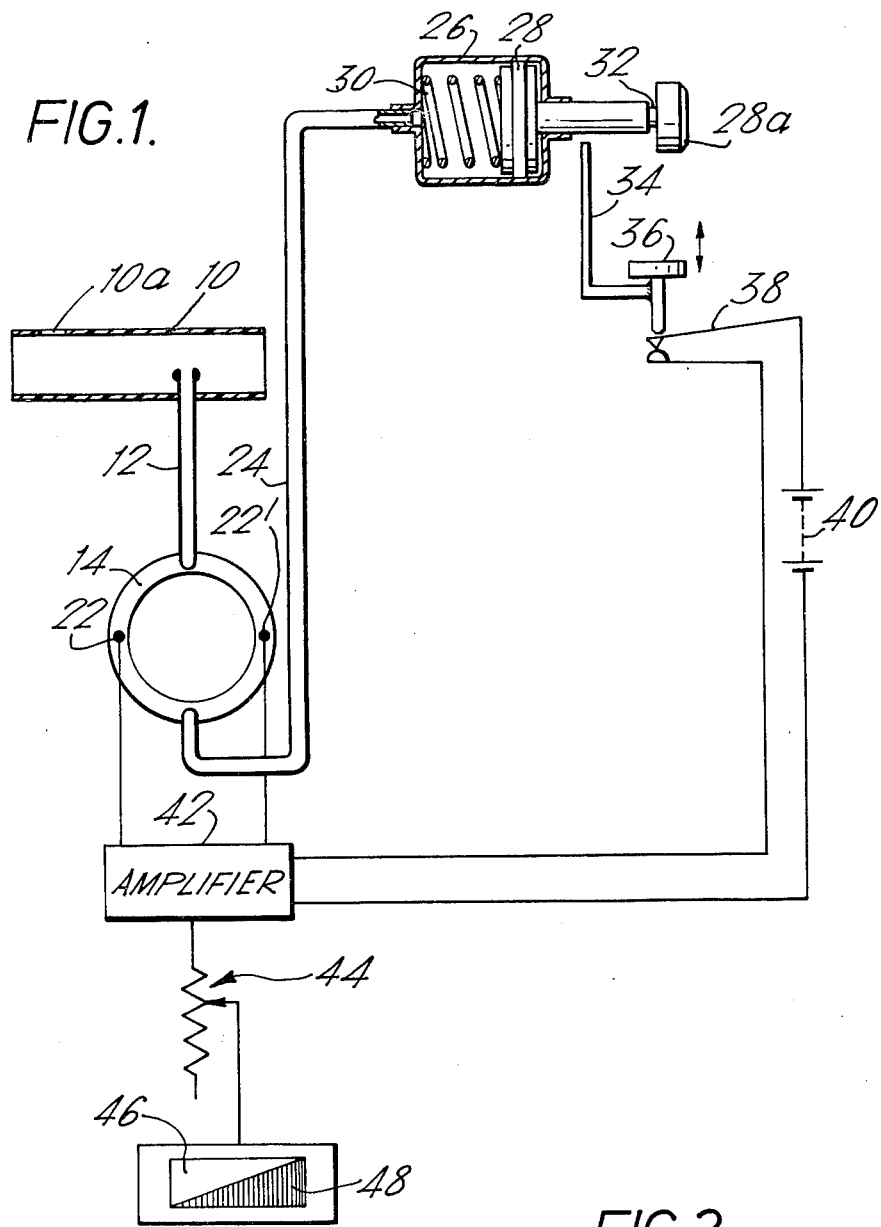
FIG. 1 is a diagrammatic representation of apparatus for measuring blood alcohol constructed in accordance with the present invention.
Figure 2:
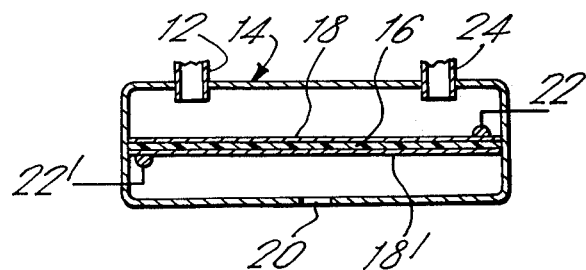
FIG. 2 is a section through a fuel cell sensor suitable for use in the meter of FIG. 1.

The tube 10 has leading radially into it one end of a pipe 12. The other end of pipe 12 leads to one side of a sensor in the form of a fuel cell generally indicated at 14 and shown in greater detail in FIG. 2. The fuel cell 14 consists of a thin sheet 16 of a porous material such as glass, ceramic or plastic which is coated on both sides with layers 18, 18' of one or any combination of the following metals; namely gold, silver, platinum, palladium or their alloys. The porous sheet 16 contains an electrolyte of phosphoric acid and/or sodium hydroxide. The layers 18, 18' act as the anode and the cathode of the cell 14 and the cell is contained in a housing which has an opening 20 so that the layer 18' is in constant contact with the atmosphere. The layers 18, 18' are also connected to electrodes 22, 22' from which the potential generated by the cell can be measured.

The surface of the layer 18 is connected via a pipe 24 to a piston and cylinder arrangement indicated at 26. The piston 28 of this piston and cylinder arrangement 26 is biased by resilient means, here a compression spring 30. The piston 28 also has a groove 32 arranged to co-operate with a latch 34 so that the piston 28 can be held in a depressed position with the spring 30 compressed by the latch 34. A further press switch 36 is connected to the latch 34 and is also arranged to act upon a pair of electrical contacts 38 so that depression of the switch 36 releases the latch 34 and closes the contacts 38 thus completing an electrical circuit between a battery 40 and an operational amplifier 42 also connected to the electrodes 22, 22'. The output of the operational amplifier 42 is taken via a potentiometer 44 to a microameter 46. The microameter 46 has a taut suspension movement, the relatively small angle of deflection being amplified by means of a drum partly shown at 46 which has a spiral line 48 marked on it, thus giving an analogue display of the output from the operational amplifier. The meter 46 can be calibrated to indicate the amount of alcohol in the gas sample, or it may be arranged to indicate whether the amount of alcohol in a sample exceeds a predetermined value.

When in operation, the piston 28 is depressed and held in this position by the latch 34. The tube 10 is fitted to the pipe 12 and the subject asked to blow through it. Because of the open end of the tube 10 and the aperture 10a, the tube acts as a whistle thus providing an indication that the subject is blowing. It has been found that with a low resistance system of this kind, it is easy to get a discard volume of a liter in practically all cases and in most cases 2 liters or more can be obtained. As the subjects level of exhalation starts to decrease as indicated from the sound of the whistle the switch 36 is pressed releasing the latch 34. The compressed spring 30 pushes the piston 28 thus drawing air from the tube 10 via the pipe 12 into the fuel cell 14 so that this sample of air comes into turbulent contact with the layer 18 of the fuel cell 14. A potential is thus generated in the cell by the oxidation of any alcohol at this electrode and the reduction of oxygen at the other electrode. At the same time as the release of the piston 28 the switch 36 closes the contacts 38 so that a reading of the potential generated can be obtained from the microameter 46. The output from the fuel cell 14 rises to a peak in a few seconds but takes about 3 minutes to decay to a point at which the rate of change is slow enough for another reading to be taken. The tube 10 is not essential, the same effect could be obtained by asking the subject to breathe over the open end of the pipe 12.

If necessary a zeroing device can be fitted for the display, such as by providing a switch which is arranged to short circuit the electrodes 18, 18' and to open circuit the electrodes before a reading is taken. Such a switch could be operated by the switch 36. The sensitivity can be adjusted and is normally set by the calibration potentiometer 44 so that the microameter reads 50% of full scale at the limit level. This makes readings of sufficient precision quite easy and enables readings up to twice the limit to be measured. If it is felt desirable to make any different readings above this level a divide by two button can be supplied.

In the cell described the air side of the fuel cell, i.e., that formed by layer 18' acts as an oxygen electrode which imposes a constant power potential, so that oxidation of alcohol does not proceed beyond acetic acid making the system reasonably specific for alcohol in breath. In particular it is not sensitive to acetone or hydrocarbons such as petrol.

While apparatus has been described using a sensor in the form of a fuel cell other suitable electrochemical sensors can be used such as a polarographic cell or a voltaic cell, or semiconductor or catalytic sensors.

The valve system has the important advantage that it introduces to the sensor a small, precise and reproducible volume of gas to the sensor. In addition the apparatus is simple in operation merely requiring the operation of the push button 28a to set the apparatus and the operation of switch 36 to sample the gas and provide the output indication on meter 46.

Furthermore the apparatus can be made such a size that it can easily be carried in an inside pocket or better still in a small holster next to the skin. This ensures that temperature is maintained at a sufficiently high and constant level to ensure constant calibration and avoid excessive condensation or moisture in the air passages. There is no need for a heated sampling system as breath is sucked directly into the sensor. Although the apparatus has been described embodying an analogue display device 46, it is possible to substitute a digital display device for the analogue device.

Finally, current is only drawn from the battery 20 when actually taking a reading so that the latter has virtually its shelf life and provided it is renewed regularly there is no need for a voltage checking system.

Although the description hereinbefore has been solely concerned with the detection of alcohol in breath naturally it may be possible to have other fuel cells which could detect other contaminants in other gasses, thus extending the utility of the meter.

We claim:

1. Apparatus for detecting alcohol vapour in a gas and particularly for detecting alcohol vapour in exhaled breath, comprising a fuel cell, said fuel cell having inlet means for interposition in an intermediate position of a low resistance path along which breath is exhaled, said low resistance path comprising a tube including an inlet for receiving said gas, a first outlet for detachable connection to the inlet means and a vent port for venting at least some of the gas to atmosphere, means serially communicating with said inlet means through said fuel cell and actuable for drawing a predetermined sample volume of gas from the exhaled breath stream into said fuel cell, said fuel cell further including means for providing an electrical output signal dependent upon the amount of alcohol vapour in the gas sample, and measuring means coupled to the sensor output for measuring the magnitude of said electrical output signal.

2. Apparatus as claimed in claim 1, in which said tube is open ended with its inlet being at one end thereof, said first outlet being intermediate said ends, said inlet means being a pipe inserted through said first outlet partially into said tube and connected to said fuel cell.

3. Apparatus as claimed in claim 1 in which the tube includes means defining an aperture open to the atmosphere intermediate to the tube ends for defining a whistle wherein a change in sound of the whistle warns of decreasing exhalation into the tube, and including means actuable upon said changes for both initiating expansion of said chamber means and applying operating potential to said measuring means whereby measurement of alcohol content can be reliably carried out during the latter portion of an exhalation, said tube providing a low resistance to said exhalation for maximizing exhalation volume.

4. Apparatus for detecting alcohol vapour in a gas and particularly for detecting alcohol vapour in exhaled breath, comprising a fuel cell, said fuel cell having inlet means for interposition in an intermediate position of a low resistance path along which breath is exhaled, means serially communicating with said inlet means through said fuel cell and actuable for drawing a predetermined sample volume of gas from the exhaled breath stream into said fuel cell, said drawing means comprising a cylinder, a piston slidably mounted in the cylinder, a gas communicating means connected between the cylinder and fuel cell, and resilient means for biasing the piston in one direction, said fuel cell further including means for providing an electrical output signal dependent upon the amount of alcohol vapour in the gas sample, and measuring means coupled to the sensor output for measuring the magnitude of said electrical output signal.

5. Apparatus as claimed in claim 4, further comprising latch means for maintaining the resilient means in a stressed state whereby the piston is in one predetermined position and means for releasing the resilient means whereby, in operation, the piston is moved to a second predetermined position and the said predetermined volume of gas is introduced into the fuel cell.

6. Apparatus as claimed in claim 5, further comprising a source of electrical energy, in which the measuring means includes electrically-operated amplifier means and the releasing means includes switch means for connecting the source to the electrically-operated amplifier means.

7. In apparatus for detecting alcohol vapour in a gas including a sensor for providing an electrical output signal dependent upon the amount of alcohol present in a gas sample introduced into it; and means introducing a predetermined volume of a gas sample into the sensor comprising, a cylinder having a gas port formed therein, a gas communicating means connecting between the gas port and a port in the sensor, a piston slideably mounted in said cylinder between first and second limiting positions, and means resiliently biasing the piston towards said second position, latch means for maintaining the piston in its first position against the bias of the resilient means, and means for releasing the latch means and thereby for introducing the said predetermined volume of gas into the sensor as the piston is moved to its second position by said resilient means.

8. Apparatus as claimed in claim 7, including a source of electrical energy, an amplifier connected to the electrical output of the sensor and a switch closable to energize the amplifier from the electrical energy source, said latch means and piston including interengageable detent means releaseable for permitting said piston to move to its second position, said means for releasing comprising manually actuable means coupled to said switch actuable for separating said detent means and simultaneously closing said switch, whereby to cause said piston to draw a gas sample into said sensor and simultaneously energize said amplifier.

9. Apparatus as claimed in claim 8, including an open-ended tube for receiving exhaled breath at one end and providing a low resistance path therethrough to the atmosphere, said sensor including an open-ended inlet pipe transversely and partially extending into an intermediate portion of said tube to enable drawing of breath from said tube upon release of said piston, and whistle means on said tube responsive to a decrease in exhalation flow for signaling a preferred time for actuation of said manually actuable means.

\* \* \* \* \*